US010730971B2

(12) United States Patent
Zuideveld et al.

(10) Patent No.: US 10,730,971 B2
(45) Date of Patent: Aug. 4, 2020

(54) PROCATALYST FOR POLYMERIZATION OF OLEFINS COMPRISING AN AMINOBENZOATE INTERNAL DONOR AND A 1,3-DIETHER INTERNAL DONOR IN A SPECIFIC RATIO

(71) Applicant: SABIC Global Technologies B.V., Bergen op Zoom (NL)

(72) Inventors: Martin Alexander Zuideveld, Kelmis (BE); Sergei Andreevich Sergeev, Novosibirsk (RU); Vladimir Aleksandrovich Zakharov, Novosibirsk (RU); Dafne Lise Steinfort, Sittard (NL)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 15/736,878

(22) PCT Filed: Jun. 17, 2016

(86) PCT No.: PCT/EP2016/064082
§ 371 (c)(1),
(2) Date: Dec. 15, 2017

(87) PCT Pub. No.: WO2016/203017
PCT Pub. Date: Dec. 22, 2016

(65) Prior Publication Data

US 2018/0362674 A1     Dec. 20, 2018

(30) Foreign Application Priority Data

Jun. 19, 2015 (EP) ..................... 15172899

(51) Int. Cl.
| C08F 4/649 | (2006.01) |
| C08F 4/654 | (2006.01) |
| C08F 10/06 | (2006.01) |
| C07C 233/69 | (2006.01) |
| C08F 110/06 | (2006.01) |

(52) U.S. Cl.
CPC ............ *C08F 10/06* (2013.01); *C07C 233/69* (2013.01); *C08F 110/06* (2013.01)

(58) Field of Classification Search
CPC .......... C08F 4/649; C08F 4/654; C08F 4/655; C08F 110/06
See application file for complete search history.

(56) References Cited

U.S. PATENT DOCUMENTS

| 4,414,132 A | 11/1983 | Goodall et al. |
| 4,978,648 A | 12/1990 | Barbe et al. |
| 5,077,357 A | 12/1991 | Job |
| 5,106,806 A | 4/1992 | Job |
| 5,556,820 A | 9/1996 | Funabashi et al. |

FOREIGN PATENT DOCUMENTS

| EP | 1283222 A1 | 2/2003 |
| EP | 1222214 B1 | 7/2004 |
| WO | 9632427 A1 | 10/1996 |
| WO | 0123441 A1 | 4/2001 |

(Continued)

OTHER PUBLICATIONS

Bartoli et al., "Convenient Procedure for the Reduction of β-Enamino Ketones: Synthesis of γ-Amino Alcohols and Tetrahydro-1,3-oxazines", Journal of the Chemical Society, vol. 1, No. 5, 1994, 7 pages.
International Search Report for International Application No. PCT/EP2016/064082; International Filing Date Jun. 17, 2016, dated Sep. 29, 2016, 2 pages.
Pasquini, N, "Polypropylene Handbook", 2nd edition, Chapter 6.2, 2005, 11 Pages.
Pullukat et al., "Silica-Based Ziegler-Natta Catalysts: A Patent Review", Catal. Rev.-Sci. Eng., 41(3&4). 1999, 40 pages.
Ser van der Ven, "Polypropylene and other Polyolefins: Polymerization and Characterization," Studies in Polymer Science 7, 1990, 3 pages.

(Continued)

*Primary Examiner* — Caixia Lu
(74) *Attorney, Agent, or Firm* — Cantor Colburn LLP

(57) ABSTRACT

A process for preparing a procatalyst for polymerization of olefins, comprising contacting a magnesium-containing support with a halogen-containing titanium compound, a first internal electron donor represented by Formula A, a second internal electron donor represented by Formula B, and an activator; wherein the molar ratio of the first internal donor to the second internal donor is between 0.01 and 0.7;

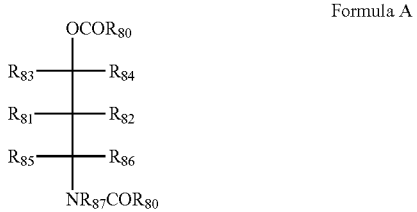

Formula A

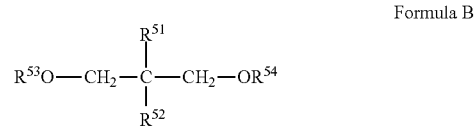

Formula B wherein in Formula A each $R^{80}$ group is independently a substituted or unsubstituted aromatic group; and $R^{81}$, $R^{82}$, $R^{83}$, $R^{84}$, $R^{85}$, $R^{86}$ and $R^{87}$ are each independently selected from a hydrogen or a hydrocarbyl group; wherein in Formula B $R^{51}$ and $R^{52}$ are each independently selected from a hydrogen or a hydrocarbyl group; and $R^{53}$ and $R^{54}$ are each independently selected from hydrogen, a halide or a hydrocarbyl group.

19 Claims, No Drawings

(56) References Cited

FOREIGN PATENT DOCUMENTS

| WO | 2007134851 A1 | 11/2007 |
| WO | 2014001257 A1 | 1/2014 |
| WO | 2014118164 A1 | 8/2014 |
| WO | 2014118165 A1 | 8/2014 |
| WO | 2015185490 A1 | 12/2015 |

OTHER PUBLICATIONS

White, "Deamination of Amines. 2-Phenylethyl Benzoate via the Nitrosoamide Decomposition," Organic Syntheses, vol. 5, p. 336, 1973; vol. 47, p. 44, 1967; 5 pages.

Written Opinion for International Application No, PCT/EP2016/064082; International Filing Date Jun. 17, 2016, dated Sep. 29, 2016, 5 pages.

PROCATALYST FOR POLYMERIZATION OF OLEFINS COMPRISING AN AMINOBENZOATE INTERNAL DONOR AND A 1,3-DIETHER INTERNAL DONOR IN A SPECIFIC RATIO

This application is a national stage application of PCT/EP2016/064082 filed Jun. 17, 2016, which claims priority to European Patent Application 15172899.5 filed Jun. 19, 2015, both of which are hereby incorporated by reference in their entirety.

The present invention relates to a process for preparing a procatalyst comprising a butyl magnesium support contacted with a titanium halide compound, an aminobenzoate internal donor, a 1,3-diether internal donor and an activator. The present invention also relates to the procatalyst obtained via said process. Furthermore, the invention is directed to a catalyst system for polymerization of olefins comprising the procatalyst, a co-catalyst and an external electron donor; a process of making polyolefins by contacting at least one olefin with said catalyst system and to polyolefins obtainable by said process.

Catalyst systems and their components that are suitable for preparing a polyolefin are generally known. One type of such catalysts are generally referred to as Ziegler-Natta catalysts. An overview of such catalyst types is for example given by T. Pullukat and R. Hoff in Catal. Rev.—Sci. Eng. 41, vol. 3 and 4, 389-438, 1999. The preparation of such a procatalyst is for example disclosed in WO96/32427 A1.

It is known that the molecular weight distribution (MWD) influences the properties of polyolefins and as such influences the end-uses of a polymer. There is a need in the industry for catalyst that are able to provide polyolefins having an intermediate or medium MWD which have a general purpose application. There is, an on-going need in industry for phthalate free polymers. There is also an on-going need in industry for catalysts showing better performance, e.g. higher activity, good yield, good control of stereochemistry, good isotacticity, good hydrogen sensitivity and/or lower amount of xylene solubles (XS).

It is thus an object of the invention to provide an improved procatalyst for polymerization of olefins, especially polypropylene, which procatalyst allows obtaining of polyolefins with intermediate molecular weight distribution, low XS values and high productivity. One or more of the aforementioned objects of the present invention are achieved by the various aspects of the present invention.

SUMMARY OF THE INVENTION

The present invention is related to the use of a combination of an aminobenzoate internal electron donor and a 1,3-diether internal electron donor in a ratio of between 0.01 and 0.7, combined with an activator using a butyl magnesium support. It has surprisingly been found by the present inventors that the combination of a butyl magnesium support, two internal electron donors in a specific molar ratio together with an activator according to the present invention allows the production of polymers having an intermediate MWD and low XS values while allowing good yield and good hydrogen sensitivity.

The invention relates to a process for preparing a procatalyst for polymerization of olefins, comprising contacting a magnesium-containing support with a halogen-containing titanium compound, a first internal electron donor represented by Formula A, a second internal electron donor represented by Formula B, and an activator; wherein the molar ratio of the first internal electron donor to the second internal electron donor is between 0.01 and 0.7;

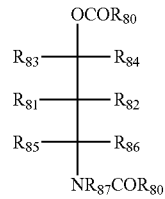

Formula A

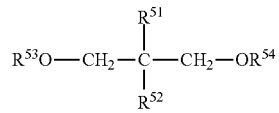

Formula B wherein in Formula A each $R^{80}$ group is independently a substituted or unsubstituted aromatic group; $R^{81}$, $R^{82}$, $R^{83}$, $R^{84}$, $R^{85}$, $R^{86}$ and $R^{87}$ are each independently selected from a hydrogen or a hydrocarbyl group; N is a nitrogen atom; O is an oxygen atom; and C is a carbon atom;

wherein in Formula B $R^{51}$ and $R^{52}$ are each independently selected from a hydrogen or a hydrocarbyl group; $R^{53}$ and $R^{54}$ are each independently selected from hydrogen, a halide or a hydrocarbyl group; O is an oxygen atom; and C is a carbon atom;

said process comprising the steps of:

i) contacting a compound $R^4_z MgX^4_{2-z}$ with an alkoxy- or aryloxy-containing silane compound to give a first intermediate reaction product, being a solid $Mg(OR^1)_x X^1_{2-x}$, wherein $R^1$ is a hydrocarbyl group, wherein $R^4$ is butyl; wherein $X^4$ and $X^1$ are each independently a halide; z is in a range of larger than 0 and smaller than 2, being 0<z<2;

ii) optionally contacting the solid $Mg(OR^1)_x X^1_{2-x}$ obtained in step ii) with at least one activating compound selected from the group formed by activating electron donors and metal alkoxide compounds of formula $M^1(OR^2)_{v-w}(OR^3)_w$ or $M^2(OR^2)_{v-x}(R^3)_w$, to obtain a second intermediate product; wherein: $M^1$ is a metal selected from the group consisting of Ti, Zr, Hf, Al or Si; v is the valency of $M^1$; $M^2$ is a metal being Si; v is the valency of $M^2$; $R^2$ and $R^3$ are each independently a hydrocarbyl group; w is smaller than v, v is preferably 3 or 4;

iii) contacting the first or second intermediate reaction product, obtained respectively in step i) or ii), with the halogen-containing Ti-compound, the first internal electron donor according to Formula A, the second internal electron donor according to Formula B, and the activator.

In an embodiment, the first internal electron donor according to Formula A is selected from the group consisting of 4-[benzoyl(methyl)amino]pentan-2-yl benzoate; 2,2,6,6-tetramethyl-5-(methylamino)heptan-3-ol dibenzoate; 4-[benzoyl (ethyl)amino]pentan-2-yl benzoate and 4-(methylamino)pentan-2-yl bis (4-methoxy)benzoate), preferably 4-[benzoyl(methyl)amino]pentan-2-yl benzoate.

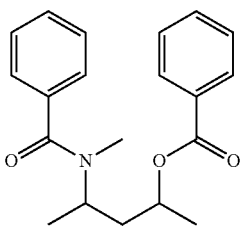

4-[benzoyl(methyl)amino]pentan-2-yl benzoate

In an embodiment, the second internal electron donor according to Formula A is selected from the group consisting of 2-isobutyl-2-isobutyl-1,3-dimethoxypropane, 2-ethyl-2-butyl-1,3-dimethoxypropane, 2-isopropyl-2-isopentyl-1,3-dimethoxypropane and 9,9-bis (methoxymethyl) fluorene, preferably 9,9-bis-methoxymethyl-fluorene.

In an embodiment, the second internal electron donor according to Formula A is selected from the group consisting of 2-isobutyl-2-isobutyl-1,3-dimethoxypropane, 2-ethyl-2-butyl-1,3-dimethoxypropane, 2-isopropyl-2-isopentyl-1,3-dimethoxypropane and 9,9-bis (methoxymethyl) fluorene, preferably 9,9-bis-methoxymethyl-fluorene.

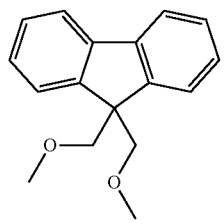

9,9-bis-methoxymethyl-fluorene

In an embodiment, a monoester activator is present selected from the group consisting of butyl formate, ethyl acetate, amyl acetate, butyl acetate, ethyl acrylate, methyl methacrylate, isobutyl methacrylate, ethyl p-methoxy benzoate, methyl p-ethoxybenzoate, ethyl p-ethoxybenzoate, ethyl benzoate, methyl benzoate, propyl benzoate, ethyl p-chlorobenzoate, ethyl p-bromobenzoate, methyl-p-toluate and ethyl-naphthate, preferably ethyl acetate, ethyl benzoate, benzoyl chloride, ethyl p-bromobenzoate, n-propyl benzoate, and benzoic anhydride, more preferably ethyl benzoate and ethyl acetate.

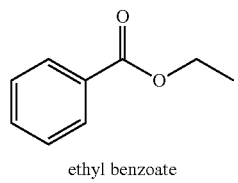

ethyl benzoate

In an embodiment, a benzamide activator is present selected from the group consisting of benzamide, N-methylbenzamide, N,N-dimethylbenzamide, N-ethylbenzamide, N,N-diethylbenzamide, N-methyl-N-ethylbenzamide, 2-(trifluormethyl)benzamide, N,N-dimethyl-2-(trifluormethyl) benzamide, 3-(trifluormethyl)benzamide, N,N-dimethyl-3-(trifluormethyl)benzamide, 2,4-dihydroxy-N-(2-hydroxyethyl)benzamide, N-(1H-benzotriazol-1-ylmethyl) benzamide, 1-(4-ethylbenzoyl)piperazine, 1-benzoyl piperidine, preferably N,N-dimethylbenzamide of N-methylbenzamide.

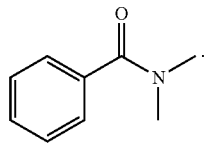

N,N-dimethylbenzamide
(BA-2Me)

In an embodiment, the first internal donor is 4-[benzoyl (methyl)amino]pentan-2-yl benzoate (AB) and the second internal donor is 9,9-bis-methoxymethyl-fluorene (Flu). In an embodiment, the first internal donor is 4-[benzoyl (methyl)amino]pentan-2-yl benzoate (AB) and the second internal donor is 9,9-bis-methoxymethyl-fluorene (Flu) and the activator is the monoester ethylbenzoate. In an embodiment, the first internal donor is 4-[benzoyl(methyl)amino] pentan-2-yl benzoate (AB) and the second internal donor is 9,9-bis-methoxymethyl-fluorene (Flu) and the activator is the benzamide compound N,N-dimethylbenzamide (BA-2Me). In an embodiment, the first internal donor is 4-[benzoyl(methyl)amino]pentan-2-yl benzoate (AB), the second internal donor is 9,9-bis-methoxymethyl-fluorene (Flu), the monoester activator is ethylbenzoate (EB); the ratio between the first internal donor and the second internal donor is between 0.01 and 0.7. In an embodiment, the first internal donor is 4-[benzoyl(methyl)amino]pentan-2-yl benzoate (AB), the second internal donor is 9,9-bis-methoxymethyl-fluorene (Flu), the benzamide activator is N,N-dimethylbenzamide (BA-2Me); the ratio between the first internal donor and the second internal donor is between 0.01 and 0.7.

In an embodiment, during step ii) an alcohol, e.g. ethanol, is used as activating electron donor and titanium tetraalkoxide is used as metal alkoxide compound.

In an embodiment, the process comprises the steps of: i) contacting butylmagnesiumchloride with tetraethoxysilane to give said first intermediate reaction product; ii) contacting said first intermediate reaction product with ethanol as activating electron donor and titanium tetraethoxide as metal alkoxide compounds to obtain a second intermediate reaction product; iii) contacting the second intermediate reaction product with titanium tetrachloride, 4-[benzoyl(methyl) amino]pentan-2-yl benzoate as the first internal donor, 9,9-bis-methoxymethyl-fluorene as the second internal donor, and ethylbenzoate as the activator. In a specific embodiment, step iii) comprises three stages (I, II and III) of adding titanium tetrachloride wherein 4-[benzoyl(methyl)amino] pentan-2-yl benzoate, 9,9-bis-methoxymethyl-fluorene, and ethylbenzoate are each added during stage I. In a specific embodiment, step iii) comprises three stages (I, II and III) of adding titanium tetrachloride wherein 4-[benzoyl(methyl) amino]pentan-2-yl benzoate is added during stage II, 9,9-bis-methoxymethyl-fluorene is added during stage III, and ethylbenzoate is added during stage I.

In an embodiment, the process comprises the steps of: i) contacting butylmagnesiumchloride with tetraethoxysilane to give said first intermediate reaction product; ii) contacting said first intermediate reaction product with ethanol as activating electron donor and titanium tetraethoxide as metal alkoxide compounds to obtain a second intermediate reaction product; iii) contacting the second intermediate reaction product with titanium tetrachloride, 4-[benzoyl(methyl)

amino]pentan-2-yl benzoate as the first internal donor, 9,9-bis-methoxymethyl-fluorene as the second internal donor, and N,N-dimethylbenzamide (BA-2Me) as the activator. In a specific embodiment, step iii) comprises three stages (I, II and III) of adding titanium tetrachloride wherein 4-[benzoyl (methyl)amino]pentan-2-yl benzoate, 9,9-bis-methoxymethyl-fluorene, and N,N-dimethylbenzamide (BA-2Me) are all added during stage I. In a specific embodiment, step iii) comprises three stages (I, II and III) of adding titanium tetrachloride wherein 4-[benzoyl(methyl)amino]pentan-2-yl benzoate is added during stage II, 9,9-bis-methoxymethyl-fluorene is added during stage III, and N,N-dimethylbenzamide is added during stage I.

In another aspect, the present invention relates to a procatalyst obtained by or obtainable by a process according to the invention. In another aspect, the present invention relates to a catalyst system for the polymerization of olefins, comprising a procatalyst according to the present invention; a co-catalyst; and an external donor. In another aspect, the present invention relates to a process for preparing a polyolefin by contacting an olefin with the catalyst system according to the present invention; the olefin being preferably propylene. In another aspect, the present invention relates to a polyolefin, preferably polypropylene, obtained by or obtainable by the process according to the present invention; said polyolefin preferably having a $M_w/M_n$ of between 4.5 and 6.5.

These aspects and embodiments will be described in more detail below.

Definitions

The following definitions are used in the present description and claims to define the stated subject matter. Other terms not cited below are meant to have the generally accepted meaning in the field.

"Ziegler-Natta catalyst" as used in the present description means: a transition metal-containing solid catalyst compound (also typically referred to as a procatalyst) comprising a transition metal halide (selected from titanium halide, chromium halide, hafnium halide, zirconium halide, and vanadium halide), supported on a metal or metalloid compound (e.g. a magnesium compound or a silica compound); an organometallic compound (also typically referred to as a co-catalyst) and optionally one or more electron donor compounds (e.g. external electron donors).

"Ziegler-Natta catalytic species" or "catalytic species" as used in the present description means: a transition metal-containing species comprises a transition metal halide (selected from titanium halide, chromium halide, hafnium halide, zirconium halide and vanadium halide).

"internal donor" or "internal electron donor" or "ID" as used in the present description means: an electron-donating compound containing one or more atoms of oxygen (O) and/or nitrogen (N). This ID is used as a reactant in the preparation of a solid procatalyst.

"external donor" or "external electron donor" or "ED" as used in the present description means: an electron-donating compound used as a reactant in the polymerisation of olefins. An ED is a compound added independent of the procatalyst. It is not added during procatalyst formation.

"activator" as used in the present description means: an electron-donating compound containing one or more atoms of oxygen (O) and/or nitrogen (N) which is used to during the synthesis of the procatalyst prior to the addition of an internal donor.

"activating compound" as used in the present description means: a compound used to activate the solid support prior to contacting it with the catalytic species.

"modifier" or "Group 13- or transition metal modifier" as used in the present description means: a metal modifier comprising a metal selected from the metals of Group 13 of the IUPAC Periodic Table of elements and transition metals.

"procatalyst" as used in the present description means: a component of a catalyst composition generally comprising a solid support, a transition metal-containing catalytic species and one or more internal donors.

"halide" or "halogen" as used in the present description means: an ion selected from the group of: fluoride (F—), chloride (Cl—), bromide (Br—) or iodide (I—).

"heteroatom" as used in the present description means: an atom other than carbon or hydrogen, preferably F, Cl, Br, I, N, O, P, B, S or Si.

"hydrocarbyl" as used in the present description means: a substituent containing hydrogen and carbon atoms. It may be linear, branched or cyclic. It may be saturated or unsaturated. It may be selected alkyl, alkenyl, aryl, aralkyl, alkoxycarbonyl or alkylaryl groups, and one or more combinations thereof; preferably alkyl, alkenyl, aryl, aralkyl, or alkylaryl groups. It hence may be an aliphatic radical, such as alkyl, alkenyl, alkadienyl and alkynyl; an alicyclic radical, such as cycloalkyl, cycloalkadienyl cycloalkenyl; an aromatic radical, such as monocyclic or polycyclic aromatic radical, as well as combinations thereof, such as alkaryl and aralkyl. A "substituted hydrocarbyl" is a hydrocarbyl group that is substituted with one or more non-hydrocarbyl substituent groups, such as a heteroatom. Preferably, said hydrocarbyl group has 1 to 20 carbon atoms.

"alkyl" as used in the present description means: an alkyl group being a functional group or side-chain consisting of carbon and hydrogen atoms having only single bonds. An alkyl group may be straight or branched and may be un-substituted or substituted.

"aryl" as used in the present description means: an aryl group being a functional group or side-chain derived from an aromatic ring. An aryl group and may be un-substituted or substituted with straight or branched hydrocarbyl groups. An aryl group also encloses alkaryl groups wherein one or more hydrogen atoms on the aromatic ring have been replaced by alkyl groups. An "aralkyl" as used in the present description means: an arylalkyl group being an alkyl group wherein one or more hydrogen atoms have been replaced by aryl groups.

"alkoxide" or "alkoxy" as used in the present description means: a functional group or side-chain obtained from a alkyl alcohol. It consist of an alkyl bonded to a negatively charged oxygen atom.

"aryloxide" or "aryloxy" or "phenoxide" as used in the present description means: a functional group or side-chain obtained from an aryl alcohol. It consist of an aryl bonded to a negatively charged oxygen atom.

"Grignard reagent" or "Grignard compound" as used in the present description means: a compound or a mixture of compounds of formula $R_zMgX_{2-z}$ (R is a hydrocarbyl group, $0<z<2$, X is a halide) or it may be a complex having more Mg clusters, e.g. $R_4Mg_3Cl_2$.

"MWD" or "Molecular weight distribution" as used in the present description means: the ratio of the weight-average molecular weight (Mw) to the number average molecular weight (Mn), viz. $M_w/M_n$. It is used as a measure of the broadness of molecular weight distribution of a polymer.

"XS" or "xylene soluble fraction" as used in the present description means: the weight percentage (wt %) of soluble xylene in the polymer product.

"production rate" or "yield" as used in the present description means: the amount of kilograms of polymer produced per gram of procatalyst consumed in the polymerization reactor per hour, unless stated otherwise.

Unless stated otherwise, when it is stated that any R group is "independently selected from" this means that when several of the same R groups are present in a molecule they may have the same meaning of they may not have the same meaning. For example, for the compound $R_2M$, wherein R is independently selected from ethyl or methyl, both R groups may be ethyl, both R groups may be methyl or one R group may be ethyl and the other R group may be methyl.

DETAILED DESCRIPTION OF THE PRESENT INVENTION

The present invention is described below in more detail. All embodiments described with respect to one aspect of the present invention are also applicable to the other aspects of the invention, unless otherwise stated.

It has been surprisingly found that the procatalyst composition according to the present invention allows preparation of polyolefins, particularly of polypropylenes (PP) that have an intermediate molecular weight distribution and a low XS value in high yield. As discussed above, the present invention is related to the use of a specific solid support (prepared using a butyl Grignard) in combination with a specific combination of two internal donors (an aminobenzoate and a 1,3-diether), in a molar ratio (aminobenzoate/1,3-diether) of between 0.01 and 1 to 0.7 to 1. In other words, with an excess of the 1,3-diether.

First Internal Electron Donor (Aminobenzoate)

As a first internal electron donor a compound is used according to Formula A:

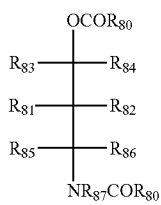

wherein in Formula A each $R^{80}$ group is independently a substituted or unsubstituted aromatic group; $R^{81}$, $R^{82}$, $R^{83}$, $R^{84}$, $R^{85}$, $R^{86}$ and $R^{87}$ are each independently selected from a hydrogen or a hydrocarbyl group; N is a nitrogen atom; O is an oxygen atom; and C is a carbon atom.

Each $R^{80}$ is preferably a aromatic group, either substituted or unsubstituted having between 6 and 20 carbon atoms. Each $R^{80}$ group may be selected from aryl or alkylaryl; optionally comprising one or more heteroatoms. It should be noted that the two $R^{80}$ groups may be the same but may also be different. $R^{80}$ can be the same or different than any of $R^{81}$-$R^{87}$. More preferably, $R^{80}$ is selected from the group consisting of $C_6$-$C_{10}$ aryl unsubstituted or substituted with e.g. an acylhalide or an alkoxyde; and $C_7$-$C_{10}$ alkaryl and aralkyl group; for instance phenyl, benzyl, 4-methoxyphenyl, 4-chlorophenyl, 4-methylphenyl, naphthyl, ortho-tolyl, para-tolyl or anisol; most preferably phenyl.

$R^{81}$, $R^{82}$, $R^{83}$, $R^{84}$, $R^{85}$, and $R^{86}$ are each independently selected from hydrogen or a hydrocarbyl group; preferably selected from alkyl, alkenyl, aryl, aralkyl, alkoxycarbonyl or alkylaryl groups, and one or more combinations thereof. Said hydrocarbyl group may be linear, branched or cyclic; it may be substituted or unsubstituted; it may comprise one or more heteroatoms; it may have from 1 to 20 carbon atoms.

More preferably, $R^{81}$, $R^{82}$, $R^{83}$, $R^{84}$, $R^{85}$, and $R^{86}$ are independently selected from a group consisting of hydrogen, $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group; even more preferably, selected from a group consisting of hydrogen, methyl, ethyl, propyl, isopropyl, butyl, tert-butyl, phenyl, trifluoromethyl and halophenyl group; most preferably hydrogen, methyl, ethyl, propyl, tert-butyl, phenyl or trifluoromethyl. Preferably, $R^{81}$ and $R^{82}$ is each a hydrogen atom; preferably, at least one of $R^{83}$ and $R^{84}$ and at least one of $R^{85}$ and $R^{86}$ is a hydrocarbyl group, such as having one carbon atom (methyl). Most preferably, when one of $R^{83}$ and $R^{84}$ and one of $R^{85}$ and $R^{86}$ is a hydrocarbyl group having at least one carbon atom, then the other one of $R^{83}$ and $R^{84}$ and of $R^{85}$ and $R^{86}$ is each a hydrogen atom and $R^{81}$ and $R^{82}$ is each a hydrogen atom.

$R^{87}$ is a hydrogen or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic; it may be substituted or unsubstituted; it may contain one or more heteroatoms; it may have from 1 to 20 carbon atoms, more preferably from 1 to 10 carbon atoms. $R^{87}$ may be the same or different than any of $R^{81}$, $R^{82}$, $R^{83}$, $R^{84}$, $R^{85}$, and $R^{86}$ with the provision that $R^{87}$ is not a hydrogen atom when $R^{81}$-$R^{87}$ are each a hydrogen atom. More preferably, $R^{87}$ is selected from a group consisting of $C_1$-$C_{10}$ straight and branched alkyl; $C_3$-$C_{10}$ cycloalkyl; $C_6$-$C_{10}$ aryl; and $C_7$-$C_{10}$ alkaryl and aralkyl group. Even more preferably, $R^{87}$ is selected from a group consisting of methyl, ethyl, propyl, isopropyl, butyl, tert-butyl, phenyl, benzyl and substituted benzyl and halophenyl group. Most preferably, $R^{87}$ is methyl, ethyl, propyl, isopropyl, benzyl or phenyl; and even most preferably, $R^{87}$ is methyl, ethyl or propyl.

The compound represented by Formula A may a compound represented by a Fischer projection of Formula A. Without being limited thereto, particular examples of the compounds of Formula A are the structures as depicted in the formula's below. For instance, the structure in Formula A may correspond to 4-[benzoyl(methyl)amino]pentan-2-yl benzoate:

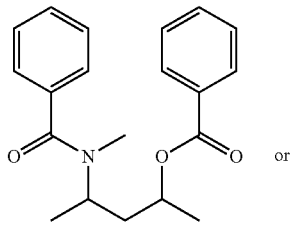

or

3-[benzoyl(cyclohexyl) amino]-1-phenylbutyl benzoate:

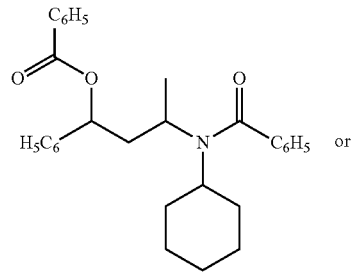

or

3-[benzoyl(propan-2-yl)amino]-1-phenylbutyl benzoate:

-continued

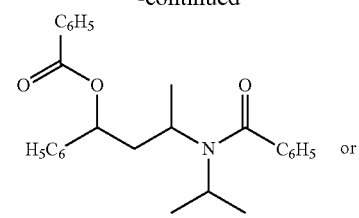

4-[benzoyl(propan-2-yl)amino]pentan-2-yl benzoate:

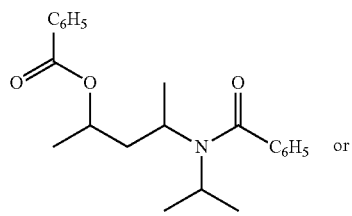

4-[benzoyl(methyl)amino]-1,1,1-trifluoropentan-2-yl benzoate:

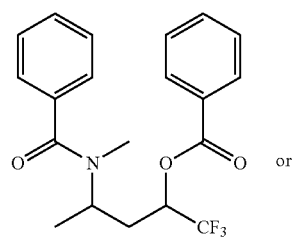

3-(methylamino)-1,3-diphenylpropan-1-ol-dibenzoate:

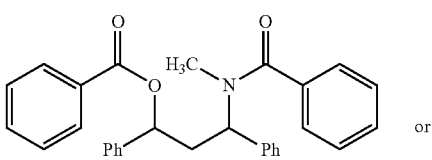

2,2,6,6-tetramethyl-5-(methylamino)heptan-3-ol dibenzoate:

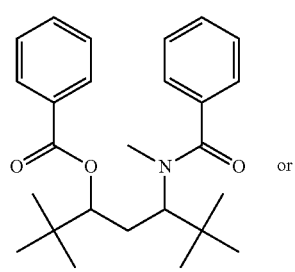

4-[benzoyl (ethyl)amino]pentan-2-yl benzoate:

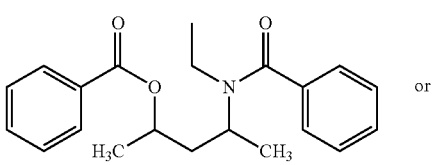

4-(methylamino)pentan-2-yl bis (4-methoxy)benzoate:

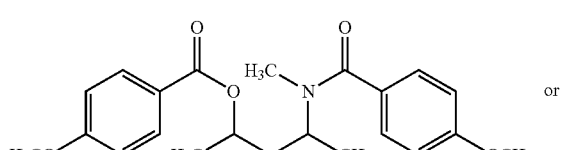

3-(methyl)amino-propan-1-ol dibenzoate:

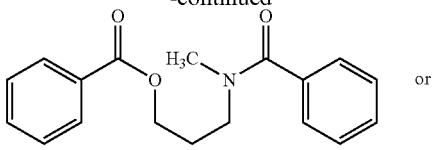

3-(methyl)amino-2,2-dimethylpropan-1-ol dibenzoate:

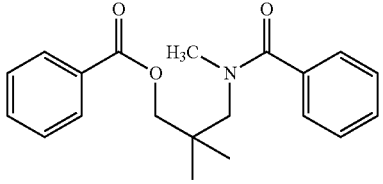

The compounds 4-[benzoyl(methyl)amino] pentan-2-yl benzoate, 3-(methylamino)-1,3-diphenylpropan-1-ol-dibenzoate, 4-[benzoyl(ethyl)amino]pentan-2-yl benzoate, and 4-(methylamino)pentan-2-yl bis (4-methoxy)benzoate are the most preferred first internal electron donors in the procatalyst according to the present invention.

The compound according to Formula A can be made by any method known in the art. In this respect, reference is made to J. Chem. Soc. Perkin trans. I 1994, 537-543 and to Org. Synth. 1967, 47, 44. These documents disclose a step a) of contacting a substituted 2,4-diketone with a substituted amine in the presence of a solvent to give a beta-enaminoketone; followed by a step b) of contacting the beta-enaminoketone with a reducing agent in the presence of a solvent to give a gamma-aminoalcohol. This synthesis is incorporated by reference. It should be noted that 4-[benzoyl(methyl)amino]pentan-yl benzoate (AB) may prepared according to the procedure described in the Examples of PCT/EP2015/062118 which is incorporated by reference. Moreover, the description of WO2014/001257 discloses more information about the synthesis of the compound according to Formula A in general, starting on page 9, line 25 to page 10, line 15 which is incorporated by reference.

Second Internal Electron Donor (1,3-Diether)

As a second internal electron donor a compound is used according to Formula B:

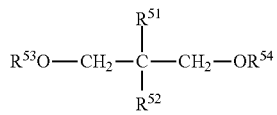

Formula B wherein $R^{51}$ and $R^{52}$ are each independently selected from a hydrogen or a hydrocarbyl group; $R^{53}$ and $R^{54}$ are each independently selected from hydrogen, a halide or a hydrocarbyl group; O is an oxygen atom; and C is a carbon atom.

As used herein a "di-ether" or a "1,3-diether" may be a 1,3-di(hydrocarboxy)propane compound, optionally substituted on the 2-position.

$R^{51}$ and $R^{52}$ are each independently selected from a hydrogen or a hydrocarbyl group selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms. Suitable examples of hydrocarbyl groups include alkyl-, cycloalkyl-, alkenyl-, alkadienyl-, cycloalkenyl-, cycloalkadienyl-, aryl-, aralkyl, alkylaryl, and alkynyl- groups.

$R^{53}$ and $R^{54}$ are each independently selected from hydrogen, a halide or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Examples of preferred 1,3-diethers are 2-isobutyl-2-isobutyl-1,3-dimethoxypropane, 2-ethyl-2-butyl-1,3-dimethoxypropane, 2-isopropyl-2-isopentyl-1,3-dimethoxypropane and 9,9-bis(methoxymethyl)fluorene. Most preferably 9,9-bis(methoxymethyl)-fluorene. More examples are disclosed on page 10 line 25—page 11 line 4 of WO2014/118164 and page 13, line 32—page 14, line 16 of WO2014/118165 which are incorporated by reference.

In an embodiment, as first internal donor is 4-[benzoyl(methyl)amino]pentan-2-yl benzoate is used and as monoester ethyl benzoate is used, a second internal electron donor according to Formula B is used. In an embodiment, as second internal donor is 9,9-bis-methoxymethyl-fluorene is used and as monoester ethyl benzoate is used, a first internal electron donor according to Formula B is used. In a further embodiment, as internal donor is 4-[benzoyl(methyl)amino]pentan-2-yl benzoate is used and as monoester ethyl benzoate is used and as second internal electron donor 9,9-bis-methoxymethyl-fluorene is used.

The internal donors according to the present invention may each independently be used in a procatalyst in an amount of between 1 and 15 wt % based on the weight of the procatalyst, preferably between 4 and 8 wt %.

The ratio between the first internal donor and the second internal donor is between 0.01 and 0.7. In an embodiment, the ratio between the first internal donor and the second internal donor is between 0.05 and 0.65, such as is between 0.1 and 0.6, preferably between 0.2 and 0.55, more preferably between 0.3 and 0.5.

Activator

Besides the two internal donors, an activator is used. Preferably, the activator is either a monoester or a benzamide compound.

The advantage of the use of an activator is that a lower amount (2-3 times) of the internal donor(s) are required when the activator is also used compared with when only the internal donors are used and no activator is used in the catalyst composition. Furthermore, the catalyst composition according to the present invention has a high hydrogen sensitivity when using an activator Monoesters may be used as activators in the present invention. The monoester according to the present invention can be any ester of a monocarboxylic acid known in the art according to Formula C: $R^{94}$—CO—$OR^{95}$. Wherein $R^{94}$ and $R^{95}$ are each independently a hydrocarbyl group such as selected from alkyl, alkenyl, aryl, aralkyl, alkoxycarbonyl or alkylaryl groups, and one or more combinations thereof. Said hydrocarbyl group may be linear, branched or cyclic; it may be substituted or unsubstituted; it may contain one or more heteroatoms; it may have from 1 to 20 carbon atoms, more preferably 1 to 10 carbon atoms, even more preferably from 1 to 8 carbon atoms, even more preferably from 1 to 6 carbon atoms. When $R^{94}$ is an aryl, this structure is according to Formula C':

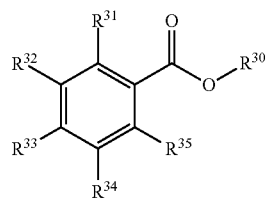

Formula C'

Wherein $R^{30}$ is a hydrocarbyl group, such as alkyl, alkenyl, aryl, aralkyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms. Suitable examples of hydrocarbyl groups include alkyl-, cycloalkyl-, alkenyl-, alkadienyl-, cycloalkenyl-, cycloalkadienyl-, aryl-, aralkyl, alkylaryl, and alkynyl- groups.

$R^{31}$, $R^{32}$, $R^{33}$, $R^{34}$, $R^{35}$ are each independently selected from hydrogen, a heteroatom (preferably a halide), or a hydrocarbyl group; such as alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Suitable examples of monoester activators according to Formula C include formates, for instance, butyl formate; acetates, for instance ethyl acetate, amyl acetate and butyl acetate; acrylates, for instance ethyl acrylate, methyl methacrylate and isobutyl methacrylate. More preferably, the aliphatic monoester is an acetate, such as ethyl acetate. Suitable examples of monoester activators according to Formula C' include C1-C20 hydrocarbyl esters of benzoic acid, such as an alkyl p-alkoxybenzoate (such as ethyl p-methoxy benzoate, methyl p-ethoxybenzoate, ethyl p-ethoxybenzoate), an alkyl benzoate (such as ethyl benzoate, methyl benzoate, propyl benzoate), an alkyl p-halobenzoate (ethyl p-chlorobenzoate, ethyl p-bromobenzoate), and benzoic anhydride. Other suitable examples include methyl-p-toluate and ethyl-naphthate. More preferably selected from ethyl benzoate, benzoyl chloride, ethyl p-bromobenzoate, n-propyl benzoate and benzoic anhydride. The monoester activator is more preferably ethyl benzoate or ethyl acetate.

The molar ratio between the monoester in step iii) and Mg may range from 0.0 to 0.5, preferably from 0.1 to 0.4, and most preferably from 0.15 to 0.25. The monoester is not used as an internal donor but as an activator.

Without to be bound by any theory, the inventors believe that the monoester used in the process according to the present invention participates at the formation of the magnesium halogen (e.g. $MgCl_2$) crystallites during the interaction of Mg-containing support with titanium halogen (e.g. $TiCl_4$). The monoester may form intermediate complexes with Ti and Mg halogen compounds (for instance, $TiCl_4$, $TiCl_3(OR)$, $MgCl_2$, MgCl(OEt), etc.), help to the removal of titanium products from solid particles to mother liquor and affect the activity of final catalyst. Therefore, the monoester according to the present invention can also be referred to as an activator.

Benzamide compounds may be used as activator in the present invention. A benzamide compound has a structure according to Formula D:

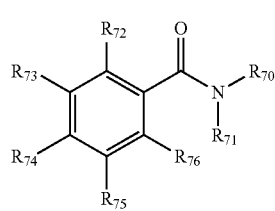

Formula D wherein $R^{70}$ and $R^{71}$ are each independently selected from hydrogen or an alkyl; wherein $R^{72}$, $R^{73}$, $R^{74}$, $R^{75}$, $R^{76}$ are each independently selected from hydrogen, a heteroatom, or a hydrocarbyl group.

Preferably, $R^{70}$ and $R^{71}$ are each independently selected from an alkyl having from 1 to 6 carbon atoms, more preferably from 1 to 3 carbon atoms. More preferably, $R^{70}$ and $R^{71}$ are each independently selected from hydrogen or methyl.

$R^{72}$, $R^{73}$, $R^{74}$, $R^{75}$, $R^{76}$ are each independently selected from hydrogen, a heteroatom (preferably a halide), or a hydrocarbyl group, selected from alkyl, alkenyl, aryl, aralkyl, alkoxycarbonyl or alkylaryl groups, and one or more combinations thereof. Said hydrocarbyl group may be linear, branched or cyclic. Said hydrocarbyl group may be substituted or unsubstituted. Said hydrocarbyl group may contain one or more heteroatoms. Preferably, said hydrocarbyl group has from 1 to 10 carbon atoms, more preferably from 1 to 8 carbon atoms, even more preferably from 1 to 6 carbon atoms.

Suitable non-limiting examples of benzamide compounds include benzamide ($R^{70}$ and $R^{71}$ are both hydrogen and each of $R^{72}$, $R^{73}$, $R^{74}$, $R^{75}$, $R^{76}$ are hydrogen) also denoted as BA-2H or N-methylbenzamide ($R^{70}$ is hydrogen; $R^{71}$ is methyl and each of $R^{72}$, $R^{73}$, $R^{74}$, $R^{75}$, $R^{76}$ are hydrogen) also denoted as BA-HMe or N,N-dimethylbenzamide ($R^{70}$ and $R^{71}$ are methyl and each of $R^{72}$, $R^{73}$, $R^{74}$, $R^{75}$, $R^{76}$ are hydrogen) also denoted as BA-2Me. Other examples include N-ethylbenzamide, N,N-diethylbenzamide, N-methyl-N-ethylbenzamide, 2-(trifluormethyl)benzamide, N,N-dimethyl-2-(trifluormethyl)benzamide, 3-(trifluormethyl)benzamide, N,N-dimethyl-3-(trifluormethyl)benzamide, 2,4-dihydroxy-N-(2-hydroxyethyl)benzamide, N-(1H-benzotriazol-1-ylmethyl) benzamide, 1-(4-ethylbenzoyl) piperazine, 1-benzoyl piperidine.

It has surprisingly been found by the present inventors that the benzamide activator having two alkyl groups (e.g. N,N-dimethylbenzamide or N,N-diethylbenzamide, preferably dimethylbenzamide) provides an even higher increase in the yield than either benzamide (BA-2H) or monoalkyl benzamide (e.g. BA-HMe). Most preferably, the activator according to the present invention is ethyl benzoate or N,N-dimethylbenzamide, most preferably dimethylbenzamide (BA-2Me).

It has surprisingly been found by the present inventors that when the benzamide activator is added during stage I of step iii) together with the catalytic species or directly after the addition of the catalytic species (e.g. within 5 minutes) an even higher increase in the yield is observed compared to when the activator is added during stage II or stage III of the process. Without wishing to be bound by a particular theory the present inventors believe that the fact that the most effective activation is obtained when the benzamide activator is added during stage I has the following reason. It is believed that the benzamide activator will bind the catalytic species and is later on substituted by the internal donor when the internal donor is added. The benzamide is not used as an internal donor but as an activator.

Process Steps for Preparing the Procatalyst

The Ziegler-Natta type procatalyst in the catalyst system according to the present invention is a magnesium-based supported catalyst, such as obtained by the process as described in WO 2007/134851 A1. In Example I the process is disclosed in more detail. Example I including all sub-examples (IA-IE) is incorporated into the present description. More details about the different embodiments are disclosed starting on page 3, line 29 to page 14 line 29. These embodiments are incorporated by reference into the present description.

The process for preparing such a procatalyst comprises the following phases: phase A): preparing a solid support for the procatalyst; phase B): optionally activating said solid support obtained in phase A) using one or more activating compounds to obtain an activated solid support; phase C): contacting said solid support obtained in phase A) or said activated solid support in phase B) with a catalytic species and optionally one or more internal donors and/or optionally an activator to obtain said procatalyst; optionally Phase D): modifying said intermediate product obtained in phase C) with a Group 13- or transition metal modifier and optionally one or more internal donors.

Phase A relates to preparing a magnesium-based solid support for the catalyst. Said magnesium-containing support is known in the art as a typical component of a Ziegler-Natta procatalyst. Synthesis of magnesium-containing supports, such as magnesium halides, magnesium alkyls and magnesium aryls, and also magnesium alkoxy and magnesium aryloxy compounds for polyolefin production, particularly of polypropylenes production are described for instance in U.S. Pat. No. 4,978,648, WO96/32427A1, WO01/23441 A1, EP1283 222A1, EP1222 21461; U.S. Pat. Nos. 5,077,357; 5,556,820; 4,414,132; 5,106,806 and 5,077,357 (incorporated by reference) but the present process is not limited to the disclosure in these documents.

Preferably, the process for preparing the solid support for the procatalyst according to the present invention comprises the following steps: step o) preparing a butyl Grignard reagent (optional) and step i) reacting a butyl Grignard reagent with a silane compound. Preferably, said Grignard reagent is a butyl magnesium chloride. A Grignard reagent may be prepared by contacting metallic magnesium with an organic halide as described in WO 96/32427 A1 and WO01/23441 A1.

Non-limiting examples of suitable silane compounds include tetramethoxysilane, tetraethoxysilane, methyltrimethoxysilane, methyltributoxysilane, phenyltriethoxysilane, diethyldiphenoxysilane, n-propyltriethoxysilane, diisopropyldi-methoxysilane, diisobutyldimethoxysilane, n-propyltrimethoxysilane, cyclohexylmethyl dimethoxysilane, dicyclopentyldimethoxy-silane, isobutylisopropyldimethoxy-silane, phenyl-trimethoxysilane, diphenyl-dimethoxysilane, trifluoropropylmethyl-dimethoxysilane, bis (perhydroisoquinolino)-dimethoxysilane, dicyclohexyldimethoxysilane, dinorbornyl-dimethoxysilane, di(n-propyl)dimethoxysilane, di(iso-propyl)-dimethoxysilane, di(n-butyl)dimethoxysilane and/or di(iso-butyl) dimethoxysilane. Preferably, tetraethoxy-silane is used as the silane compound.

Preferably, in step i) the silane-compound and the butyl Grignard compound are introduced simultaneously to a mixing device to result in particles of the first intermediate reaction product having advantageous morphology. This is for example described in WO 01/23441 A1. Here, 'morphology' does not only refer to the shape of the particles of the solid Mg-compound and the catalyst made therefrom, but also to the particle size distribution (also characterized as span), its fines content, powder flowability, and the bulk density of the catalyst particles. Moreover, it is well known that a polyolefin powder produced in polymerization process using a catalyst system based on such procatalyst has a similar morphology as the procatalyst (the so-called "replica effect"; see for instance S. van der Ven, Polypropylene and other Polyolefins, Elsevier 1990, p. 8-10). Accordingly, almost round polymer particles are obtained with a length/diameter ratio (l/D) smaller than 2 and with good powder flowability. The Si/Mg molar ratio during step i) may range from 0.2 to 20. Preferably, the Si/Mg molar ratio is from 0.4 to 1.0. The present inventors have found that when using the compounds according to the present invention the morphology of the support is maintained in turn leading to polymers having the same morphology. Moreover, the particle size distribution was also good.

Phase B relates to the optional step of activating said solid support and comprises step ii), being contacting the solid support with at least one activating compound selected from the group formed by activating electron donors and activating metal alkoxide compounds. The advantage of the use of this activation step prior to contacting the solid support with the catalytic species (process phase C) is that a higher yield of polyolefins is obtained per gram of the procatalyst. Moreover, the ethylene sensitivity of the catalyst system in the copolymerisation of propylene and ethylene is also increased because of this activation step. This activation step is disclosed in detail in WO2007/134851 of the present applicant.

Examples of suitable activating electron donors are an alcohol, like ethanol or hexanol, or an ester compound, like ethyl acetate, ethylbenzoate or a phthalate ester, or an ether, like dibutylether, or pyridine. Examples of suitable metal alkoxide compounds for use in step ii) are tetraethoxy silane or tetraethoxy titanium. Preferably, a Ti-based compound, for example titanium tetraethoxide, is used together with an activating electron donor compound. In an embodiment, during step ii) as activating compounds an alcohol is used as activating electron donor and titanium tetraalkoxide is used as metal alkoxide compound.

Phase C relates to the contacting of the support with a catalytic species and optionally one or more internal donors and/or one or more activators. Phase C may comprise several stages. During each of these consecutive stages the solid support is contacted with said catalytic species. In other words, the addition or reaction of said catalytic species may be repeated one or more times. When in phase D which is optional, an internal donor is added, it is not essential that a donor is also added during phase C.

For example, during stage I of phase C said solid support (first intermediate) or the activated solid support (second intermediate) is first contacted with said catalytic species and optionally subsequently with one or more internal donors. When a second stage is present, during stage II the intermediate product obtained from stage I will be contacted with additional catalytic species which may the same or different than the catalytic species added during the first stage and optionally one or more internal donors. In case three stages are present, stage III is preferably a repetition of stage II or may comprise the contacting of the product obtained from phase II with both a catalytic species (which may be the same or different as above) and one or more internal donors. In other words, an internal donor may be added during each of these stages or during two or more of these stages. When an internal donor is added during more than one stage it may be the same or a different internal donor. In an embodiment, step iii) comprises several stages and the internal donor according to Formula A is added in a earlier stage that the internal donor according to Formula B. In an embodiment, step iii) comprises several stages and the internal donor according to Formula B is added in a earlier stage that the internal donor according to Formula A. In an embodiment, step iii) comprises three stages (I, II and III) wherein an activator is added during stage I, the internal donor according to Formula A is added during stage II and the internal donor according to Formula B is added during stage III. In an embodiment, step iii) comprises three stages (I, II and III) wherein an activator is added during stage I, the internal donor according to Formula B is added during stage II and the internal donor according to Formula A is added during stage III.

An activator according to the present invention—if used—may be added either during stage I or stage II or stage III of phase C. An activator may also be added during more than one stage. Examples of suitable activators are benzamide compounds and monoesters, such as alkylbenzoates, such as benzamide, N-methylbenzamide, N,N-dimethylbenzamide, methylbenzoate, ethylbenzoate, ethyl acetate, and butyl acetate. More preferably ethylbenzoate or N,N-dimethylbenzamide, most preferably N,N-dimethylbenzamide.

In a preferred embodiment of the present invention a procatalyst is prepared based on a butyl magnesium support having the internal donors as discussed above and either ethylbenzoate or N,N-dimethylbenzamide as activator since the inventors have observed that this improves the activity of the catalyst and produces polymers having enhanced properties. The amount of activator may be adjusted experimental to provide optimum activity.

Preferably, phase C comprises reacting the solid support with a transition metal halide (e.g. titanium, chromium, hafnium, zirconium, vanadium) but preferably titanium halide and optionally an internal electron donor or activator to obtain a third intermediate product.

Phase D is optional in the present invention and may comprise modifying the third intermediate product with a metal-modifier and optionally on or more internal donors to obtain a procatalyst. The modification with Group 13- or transition metal, preferably aluminium, ensures the presence of Group 13- or transition metal in the procatalyst, in addition to magnesium (from the solid support) and titanium (from the titanation treatment). After the modification step another treatment with the catalytic species is carried out, that is very similar to phase C.

The procatalyst thus prepared can be used in polymerization of olefins using an external donor and a co-catalyst. In the process to prepare a polyolefin, a procatalyst, a co-catalyst, the external donor according to the present invention and the olefin can be contacted in any way known to the skilled person in the art; and as also described herein. For instance, the external donor in the catalyst system according to the present invention can be complexed with the cocatalyst and mixed with the procatalyst (pre-mix) prior to contact between the catalyst composition and the olefin. The external donor can also be added independently to the polymerization reactor. The procatalyst, the co-catalyst, and the external donor can be mixed or otherwise combined prior to addition to the polymerization reactor.

As external electron donors, all types of external electron donors known in the art may be used. Examples thereof are: alkylamino-alkyoxysilanes, such as diethyl-amino-triethoxysilane (DEATES); alkyl-alkoxysilanes, such as n-propyl triethoxysilane (nPTES) and n-propyl trimethoxysilane (nPTMS); imidosilanes, such as 1,1,1-triethoxy-N-(2,2,4,4-tetramethylpentan-3-ylidene) silanamine, 1,1,1-trimethoxy-N-(2,2,4,4-tetramethylpentan-3-ylidene) silanamine, and N,N,N',N'-tetramethylguanidine triethoxysilane; alkylimidosilanes, alkoxysilanes, such as dicyclopentyl dimethoxysilane, di-isopropyl dimethoxysilane, di-isobutyl dimethyoxysilane, methylcyclohexyl dimethoxysilane, n-propyl trimethoxysilane, n-propyltriethoxysilane, and dimethyl-amino triethoxysilane. Mixtures of external donors may be present and may include from about 0.1 mol % to about 99.9% mol % of a first external donor and from about 99.9 mol % to about 0.1 mol % of a second external donor.

As used herein, a "co-catalyst" is a term well-known in the art in the field of Ziegler-Natta catalysts and is recognized to be a substance capable of converting the procatalyst to an active polymerization catalyst. Generally, the co-catalyst is an organometallic compound containing a metal from group 1, 2, 12 or 13 of the Periodic System of the Elements (Handbook of Chemistry and Physics, 70th Edition, CRC Press, 1989-1990). The co-catalyst may include any compounds known in the art, such as hydrides, alkyls, or aryls of aluminum, lithium, zinc, tin, cadmium, beryllium, magnesium, and combinations thereof. The co-catalyst may be a hydrocarbyl aluminum co-catalyst, such as triisobutylaluminum, trihexylaluminum, di-isobutylaluminum hydride, dihexylaluminum hydride, isobutylaluminum dihydride, hexylaluminum dihydride, diisobutylhexylaluminum, isobutyl dihexylaluminum, trimethylaluminum, triethylaluminum, tripropylaluminum, triisopropylaluminum, tri-n-butylaluminum, trioctylaluminum, tridecylaluminum, tridodecylaluminum, tribenzylaluminum, triphenylaluminum, trinaphthylaluminum, and tritolylaluminum. In an embodiment, the cocatalyst is selected from triethylaluminum, triisobutylaluminum, trihexylaluminum, di-isobutylaluminum hydride and dihexylaluminum hydride. More preferably, trimethylaluminium, triethylaluminium, triisobutylaluminium, and/or trioctylaluminium. Most preferably, triethylaluminium (abbreviated as TEAL). The co-catalyst can also be a hydrocarbyl aluminum compound such as tetraethyl-dialuminoxane, methylaluminoxane, isobutylaluminoxane, tetraisobutyl-dialuminoxane, diethyl-aluminumethoxide, diisobutylaluminum chloride, methylaluminum dichloride, diethylaluminum chloride, ethylaluminum dichloride and dimethylaluminum chloride, preferably TEAL. The molar ratio of aluminum to titanium may be from about 5:1 to about 500:1 or from about 10:1 to about 200:1 or from about 15:1 to about 150:1 or from about 20:1 to about 100:1. The molar ratio of aluminum to titanium is preferably about 45:1. The aluminium/external donor molar ratio in the polymerization catalyst system preferably is from 0.1 to 200; more preferably from 1 to 100.

The invention further relates to a process for making a polyolefin by contacting an olefin with the catalyst system according to the present invention. The procatalyst, the co-catalyst, the external donor and the olefin can be contacted in any way known to the skilled person in the art; and as also described herein. Contacting the olefin with the catalyst system according to the present invention can be done under standard polymerization conditions, known to the skilled person in the art. See for example Pasquini, N. (ed.) "Polypropylene handbook" 2$^{nd}$ edition, Carl Hanser Verlag Munich, 2005. Chapter 6.2 and references cited therein. The polymerization process may be a gas phase, a slurry or a bulk polymerization process, operating in one or more than one reactor as disclosed in WO2014/001257, more precisely on page 19, line 25 to page 20, line 22 which section is incorporate by reference.

The olefin according to the invention may be selected from mono- and di-olefins containing from 2 to 40 carbon atoms. Suitable olefin monomers include alpha-olefins, such as ethylene, propylene, alpha-olefins having from 4 to 20 carbonatoms (viz. C4-20), such as 1-butene, 1-pentene, 1-hexene, 4-methyl-1-pentene, 1-heptene, 1-octene, 1-decene, 1-dodecene and the like; C4-C20 diolefins, such as 1,3-butadiene, 1,3-pentadiene, norbornadiene, 5-vinyl-2-norbornene (VNB), 1,4-hexadiene, 5-ethylidene-2-norbornene (ENB) and dicyclopentadiene; vinyl aromatic compounds having from 8 to 40 carbon atoms (viz. C8-C40) including styrene, o-, m- and p-methylstyrene, divinylbenzene, vinylbiphenyl, vinylnapthalene; and halogen-substituted C8-C40 vinyl aromatic compounds such as chlorostyrene and fluorostyrene.

The present invention also relates to a polyolefin, preferably a polypropylene obtained or obtainable by a process, comprising contacting an olefin, preferably propylene or a mixture of propylene and ethylene with the procatalyst according to the present invention. Preferably, the olefin is propylene or a mixture of propylene and ethylene, to result in a propylene-based polymer, such as propylene homopolymer or propylene-olefin copolymer. The olefin may an alpha-olefin having up to 10 carbon atoms, such as ethylene, 1-butene, 1-hexene, 1-heptene, 1-octene. A propylene copolymer is herein meant to include both so-called random copolymers which typically have relatively low comonomer content, e.g. up to 10 mol %, as well as so-called impact PP copolymers or heterophasic PP copolymers comprising higher comonomer contents, e.g. from 5 to 80 mol %, more typically from 10 to 60 mol %. The impact PP copolymers are actually blends of different propylene polymers; such copolymers can be made in one or two reactors and can be blends of a first component of low comonomer content and high crystallinity, and a second component of high comonomer content having low crystallinity or even rubbery properties. Such random and impact copolymers are well-known to the skilled in the art. A propylene-ethylene random copolymer may be produced in one reactor. Impact PP copolymers may be produced in two reactors: polypropylene homopolymer may be produced in a first reactor; the content of the first reactor is subsequently transferred to a second reactor into which ethylene (and optionally propylene) is introduced. This results in production of a propylene-ethylene copolymer (i.e. an impact copolymer) in the second reactor.

The present invention also relates to a polyolefin, preferably a propylene-based polymer obtained or obtainable by a process as described herein, comprising contacting propylene or a mixture of propylene and ethylene with a catalyst system according to the present invention. In one embodiment the present invention relates to the production of a homopolymer of polypropylene. Several polymer properties are discussed here. The polyolefin, preferably the polypropylene according to the present invention has a molecular weight distribution of between 3.5 and 8.0, preferably between 4.0 and 7.0, more preferably 4.5 and 6.5. The xylene soluble fraction (XS) of the polymer obtained is preferably from about 0.5 wt % to about 10 wt %, or from about 1 wt % to about 8 wt %, or from 2 to 6 wt %, or from about 1 wt % to about 5 wt %. Preferably, the xylene amount (XS) is lower than 6 wt %, preferably lower than 5 wt %, more preferably lower than 4 wt % or even lower than 3 wt % and most preferably lower than 2.7 wt %. The production rate is preferably from about 1 kg/g/hr to about 100 kg/g/hr, or from about 10 kg/g/hr to about 40 kg/g/hr.

The olefin polymer obtained in the present invention is considered to be a thermoplastic polymer. The thermoplastic polymer composition according to the invention may also contain one or more of usual additives, including stabilisers, e.g. heat stabilisers, anti-oxidants, UV stabilizers; colorants, like pigments and dyes; clarifiers; surface tension modifiers; lubricants; flame-retardants; mould-release agents; flow improving agents; plasticizers; anti-static agents; impact modifiers; blowing agents; fillers and reinforcing agents; and/or components that enhance interfacial bonding between polymer and filler, such as a maleated polypropylene, in case the thermoplastic polymer is a polypropylene composition. The skilled person can readily select any suitable combination of additives and additive amounts without undue experimentation. The amount of additives depends on their type and function; typically is of from 0 to about 30 wt %; preferably of from 0 to about 20 wt %; more preferably of from 0 to about 10 wt % and most preferably of from 0 to about 5 wt % based on the total composition. The sum of all components added in a process to form the polyolefins, preferably the propylene-base polymers or compositions thereof should add up to 100 wt %.

The thermoplastic polymer composition of the invention may be obtained by mixing one or more of the thermoplastic polymers with one or more additives by using any suitable means. Preferably, the thermoplastic polymer composition of the invention is made in a form that allows easy processing into a shaped article in a subsequent step, like in pellet or granular form. The composition can be a mixture of different particles or pellets; like a blend of a thermoplastic polymer and a master batch of nucleating agent composition, or a blend of pellets of a thermoplastic polymer comprising one of the two nucleating agents and a particulate comprising the other nucleating agent, possibly pellets of a thermoplastic polymer comprising said other nucleating agent. Preferably, the thermoplastic polymer composition of the invention is in pellet or granular form as obtained by mixing all components in an apparatus like an extruder; the advantage being a composition with homogeneous and well-defined concentrations of the nucleating agents (and other components).

The invention also relates to the use of the polyolefins, preferably the propylene-based polymers (also called polypropylenes) according to the invention in injection moulding, blow moulding, extrusion moulding, compression moulding, casting, thin-walled injection moulding. Furthermore, the invention relates to a shaped article comprising the polyolefin, preferably the propylene-based polymer according to the present invention. Injection moulding is widely used to produce articles such as for example caps and closures, batteries, pails, containers, automotive exterior parts like bumpers, automotive interior parts like instrument panels, or automotive parts under the bonnet. Extrusion is for example widely used to produce articles, such as rods, sheets, films and pipes. Thin wall injection moulding may for example be used to make thin wall packaging applications both for food and non-food segments. This includes pails and containers and yellow fats/margarine tubs and dairy cups.

It is noted that the invention relates to all possible combinations of features recited in the claims. Features described in the description may further be combined.

EXAMPLES

It should be noted that 4-[benzoyl(methyl)amino]pentanyl benzoate (AB) was prepared according to the procedure described in the Examples of PCT/EP2015/062118 which is incorporated by reference.

In the Examples below a procatalyst is prepared using the following phases:
Phase A) preparation of butyl magnesium based solid support (steps A. and B. in the Examples);
Phase B) activating said solid support (step C. in the Examples);
Phase C) contacting said activated solid support with a titanium catalytic species, an aminobenzoate internal donor, and 1,3-diether as internal donor and a monoester as activator (step D. in the Examples).

Examples 1-5 and Comparative Examples 1, 2 and 3

In these (comparative) examples a butyl Grignard support was used, AB was used as the aminobenzoate internal donor, Flue was used as the 1,3-diether internal donor and BA-2Me was used as the monoester activator.

Examples 1-5 and Comparative Examples 1, 2, and 3 were carried out in as discussed below, only differing in the ratio between AB and Flu. The total combined amount of AB+Flu is the same in each of these (comparative) examples and is stated, the ratio used is stated below.

A. Grignard Formation Step

A stirred flask, fitted with a reflux condenser and a funnel, was filled with magnesium powder (24.3 g). The flask was brought under nitrogen. The magnesium was heated at 80° C. for 1 hour, after which dibutyl ether (DBE, 150 ml), iodine (0.03 g) and n-chlorobutane (4 ml) were successively added. After the colour of the iodine had disappeared, the temperature was raised to 80° C. and a mixture of n-chlorobutane (110 ml) and dibutyl ether (750 ml) was slowly added for 2.5 hours. The reaction mixture was stirred for another 3 hours at 80° C. Then the stirring and heating were stopped and the small amount of solid material was allowed to settle for 24 hours. By decanting the colorless solution above the precipitate, a solution of butyl magnesium chloride (reaction product of step A) with a concentration of 1.0 mol Mg/l was obtained.

B. Preparation of the Intermediate Reaction Product 250 mL of dibutyl ether was introduced to a 1 L reactor fitted with a propeller stirrer and two baffles. The reactor was thermostated at 35° C. and the stirrer speed was kept at 200 rpm. Then a cooled (to 15° C.) 360 mL solution of the Grignard reaction product as prepared in A and 180 ml of a cooled (to 15° C.) solution of tetraethoxysilane (TES) in dibutyl ether (consisting of 38 ml of TES and 142 ml of DBE) were dosed into the reactor for 400 min with preliminary mixing in a minimixer of 0.15 ml volume, which was cooled to 15° C. by means of cold water circulating in the minimixer jacket. The premixing time was 18 seconds in the minimixer and the connecting tube between the minimixer and the reactor. The stirring speed in the minimixer was 1000 rpm. On the dosing completion, the reaction mixture was kept at 35° C. for 0.5 hours. Then the reactor was heated to 60° C. and kept at this temperature for 1 hour. Then the stirrer was stopped and the solid substance was allowed to settle. The supernatant was removed by decanting. The solid substance was washed three times using 300 ml of heptane. As a result, a white solid reaction product was obtained and suspended in 200 ml of heptane.

C. Preparation of the Second Intermediate Reaction Product

Support activation was carried out to obtain the second intermediate reaction product. Under an inert nitrogen atmosphere at 20° C. a 250 ml glass flask equipped with a mechanical agitator is filled with a slurry of 5 g of the reaction product of step B dispersed in 60 ml of heptane. Subsequently a solution of 0.86 ml methanol (MeOH/Mg=0.5 mol/mol) in 20 ml heptane is dosed under stirring during 1 hour. After keeping the reaction mixture at 20° C. for 30 minutes the slurry was slowly allowed to cool to 0° C. and 1.18 mL titaniumtetraethoxide (TET/Mg=0.15 mol/mol) in 20 mL of heptane was added at 0° C. and stirred for 30 min. The temperature was then raised to 30° C. and kept at that temperature for another 2 hours. Finally, the supernatant liquid is decanted from the solid reaction product which was washed once with 90 ml of heptane at 30° C.

D. Preparation of the Catalyst Component

A reactor was brought under nitrogen and of titanium tetrachloride (125 ml) was added to it. The reactor was heated to 100° C. stirring at a speed of 400±20 rpm and a suspension, containing about 5.5 g of activated support in 15 ml of heptane, was added to it under stirring. The reaction mixture was kept at 110° C. for 10 min. Then add N,N-dimethyl benzamide (BA-2M; BA-2M/Mg=0.15 mol/mol), 4-[benzoyl(methyl)amino]pentan-yl benzoate (AB) and 9,9-bis-methoxymethyl-fluorene (Flu) (AB+Flu/Mg=0.10 mol/mol in a ratio as shown below). The reaction mixture was raised in temperature to 115° C. during 115 minutes and kept for 105 min (stage I of catalyst preparation). Then the stirring was stopped and the solid substance was allowed to settle. The supernatant was removed by decanting, after which the solid product was washed with chlorobenzene (125 ml) at 100° C. for 15 min. The solid substance was allowed to settle and the supernatant was removed by decanting. Then the washing solution was removed by decanting, after which a mixture of titanium tetrachloride (62.5 ml) and chlorobenzene (62.5 ml) was added. The temperature of reaction mixture was increased to 115° C. Then the reaction mixture was kept at 115° C. for 30 min (stage II of catalyst preparation). After which the stirring was stopped and the solid substance was allowed to settle. The supernatant was removed by decanting, after which Stage II was repeated once. Then, a mixture of titanium tetrachloride (62.5 ml) and chlorobenzene (62.5 ml) was added. The reaction mixture was kept at 115° C. for 30 min (stage III of catalyst preparation), after which the solid substance was allowed to settle. The supernatant was removed by decanting and Stage III was repeated once, then the solid was washed five times using 100 ml of heptane at decreasing temperature by removing the heat source, after which the catalyst component, suspended in heptane, was obtained.

E. Polymerization of Propylene

Polymerization of propylene was carried out in a stainless steel reactor (with a volume of 0.7 l) in heptane (300 ml) at a temperature of 70° C., total pressure 0.7 MPa and hydrogen presence (55 ml) for 1 hour in the presence of a catalyst system comprising the catalyst component according to step D, triethylaluminium as the co-catalyst and n-propyltrimethoxysilane (nPTMS) as the external electron donor. The concentration of the catalyst component was 0.033 g/l; the concentration of triethylaluminium was 4.0 mmol/l; the concentration of n-propyltrimethoxysilane was 0.2 mmol/l.

The internal donors were added as follows in the internal donor feed:

0.0 mol % AB and 100.0 mol % Flu; (no first donor)=CE1
15.6 mol % AB and 84.4 mol % Flu; =Ex. 1
16.4 mol % AB and 83.6 mol % Flu; =Ex. 2
19.2 mol % AB and 80.8 mol % Flu; =Ex. 3
23.8 mol % AB and 76.2 mol % Flu; =Ex. 4
25.8 mol % AB and 74.2 mol % Flu; =Ex. 5
50.0 mol % AB and 50.0 mol % Flu; (ratio of $1^{st}$:$2^{nd}$ ID outside scope)=CE 2
100.0 mol % AB and 0.0 mol % Flu (no second donor)=CE 3

Example 6

Butyl Grignard, AB/Flu & EB

In this example a butyl Grignard support was used, AB was used as the aminobenzoate internal donor, Flu was used as the 1,3-diether internal donor and EB was used as the monoester activator.

Example 6 are carried out as follows. Steps A, B and C are carried out as disclosed in Examples 1-5 above. Step D is carried out as follows:

D'. Preparation of the Catalyst Component

A reactor was brought under nitrogen and of titanium tetrachloride (125 ml) was added to it. The reactor was heated to 90° C. and a suspension, containing about 5.5 g of activated support in 15 ml of heptane, was added to it under stirring. The reaction mixture was kept at 90° C. for 10 min. Then add ethyl benzoate (EB; EB/Mg=0.15 mol/mol), 4-[benzoyl(methyl)amino]pentan-yl benzoate (AB; AB/Mg=0.03 mol/mol) and 9,9-bis-methoxymethyl-fluorene (Flu; Flu/Mg=0.1 mol/mol). The reaction mixture was kept for 60 min (stage I of catalyst preparation). Then the stirring was stopped and the solid substance was allowed to settle. The supernatant was removed by decanting, after which the solid product was washed with chlorobenzene (125 ml) at 100° C. for 20 min. Then the washing solution was removed by decanting, after which a mixture of titanium tetrachloride (62.5 ml) and chlorobenzene (62.5 ml) was added. The temperature of reaction mixture was increased to 115° C. Then the reaction mixture was kept at 115° C. for 30 min (stage II of catalyst preparation). After which the stirring was stopped and the solid substance was allowed to settle. The supernatant was removed by decanting, after which a mixture of titanium tetrachloride (62.5 ml) and chlorobenzene (62.5 ml) was added. The reaction mixture was kept at 115° C. for 30 min (stage III of catalyst preparation), after which the solid substance was allowed to settle. The supernatant was removed by decanting and the solid was washed five times using 150 ml of heptane at 60° C., after which the catalyst component, suspended in heptane, was obtained.

Step E is carried out as discussed above under Examples 1-5

Example 7

In this example a butyl Grignard support was used, AB was used as the aminobenzoate internal donor, Flu was used as the 1,3-diether internal donor and EB was used as the monoester activator.

Example 7 is carried out as follows. Steps A, B, C, D and E are carried out as disclosed in Examples 1-5 above. However, in step D instead of Ba-2Me, ethyl benzoate (EB; EB/Mg=0.15 mol/mol) is used as monoester activator.

Comparative Example 4

Phenyl Grignard; AB/FLU & EB

In this comparative example a phenyl Grignard support was used, AB was used as the aminobenzoate internal donor, Flu was used as the 1,3-diether internal donor and EB was used as the monoester activator. This example is carried out using the following steps.

A'. Grignard Formation Step

This step was carried out as described in Example XVI of EP 1 222 214 B1.

A stainless steel reactor of 9 l volume was filled with magnesium powder (360 g). The reactor was brought under nitrogen. The magnesium was heated at 80° C. for 1 hour, after which a mixture of dibutyl ether (1 litre) and chlorobenzene (200 ml) was added. Then iodine (0.5 g) and n-chlorobutane (50 ml) were successively added to the reaction mixture. After the colour of the iodine had disappeared, the temperature was raised to 94° C. Then a mixture of dibutyl ether (1.6 litre) and chlorobenzene (400 ml) was slowly added for 1 hour, and then 4 litre of chlorobenzene was slowly added for 2.0 hours. The temperature of reaction mixture was kept in interval 98-105° C. The reaction mixture was stirred for another 6 hours at 97-102° C. Then the stirring and heating were stopped and the solid material was allowed to settle for 48 hours. By decanting the solution above the precipitate, a solution of phenyl magnesium chloride reaction product A has been obtained with a concentration of 1.3 mol Mg/l. This solution was used in the further catalyst preparation.

B'. Preparation of the First Intermediate Reaction Product

This step was carried out as described in Example XX of EP 1 222 214 B1, except that the dosing temperature of the reactor was 35° C., the dosing time was 360 min and the propeller stirrer was used. Dibutyl ether (250 ml) was introduced to a 1 liter reactor. The reactor was fitted by propeller stirrer and two baffles. The reactor was thermostated at 35° C. The solution of reaction product of step A (360 ml, 0.468 mol Mg) and 180 ml of a solution of tetraethoxysilane (TES) in dibutyl ether (DBE), (55 ml of TES and 125 ml of DBE), were cooled to 10° C., and then were dosed simultaneously to a mixing device of 0.45 ml volume supplied with a stirrer and jacket. Dosing time was 360 min. Thereafter the premixed reaction product A and the TES-solution were introduced to a reactor. The mixing device (minimixer) was cooled to 10° C. by means of cold water circulating in the minimixer's jacket. The stirring speed in the minimixer was 1000 rpm. The stirring speed in reactor was 350 rpm at the beginning of dosing and was gradually increased up to 600 rpm at the end of dosing stage. On the dosing completion the reaction mixture was heated up to 60° C. and kept at this temperature for 1 hour. Then the stirring was stopped and the solid substance was allowed to settle. The supernatant was removed by decanting. The solid substance was washed three times using 500 ml of heptane. As a result, a pale yellow solid substance, reaction product B (the solid first intermediate reaction product; the support), was obtained, suspended in 200 ml of heptane. The average particle size of support was 22 μm and a span value $[(d^{90}-d^{10})/d^{50}]$ of 0.5.

C'. Preparation of the Second Intermediate Reaction Product

Support activation was carried out as described in Example IV of WO/2007/134851 to obtain the second intermediate reaction product. In inert nitrogen atmosphere at 20° C. a 250 ml glass flask equipped with a mechanical agitator is filled with slurry of reaction product B (5 g) dispersed in heptane (60 ml). Subsequently a solution of ethanol (0.22 ml; EtOH/Mg=0.1) in heptane (20 ml) is dosed under stirring during 1 hour. After keeping the reaction mixture at 20° C. for 30 minutes, a solution of titanium tetraethoxide (0.79 ml; TET/Mg=0.1) in of heptane (20 ml) was added for 1 hour. The slurry was slowly allowed to warm up to 30° C. for 90 min and kept at that temperature for another 2 hours. Finally the supernatant liquid is decanted from the solid reaction product (the second intermediate reaction product; activated support) which was washed once with heptane (90 ml) at 30° C.

D'. Preparation of the Catalyst Component (for Comparative Example 4)

A reactor was brought under nitrogen and of titanium tetrachloride (125 ml) was added to it. The reactor was heated to 90° C. and a suspension, containing about 5.5 g of activated support in 15 ml of heptane, was added to it under stirring. The reaction mixture was kept at 90° C. for 10 min. Then add ethyl benzoate (EB; EB/Mg=0.15 mol/mol), 4-[benzoyl(methyl)amino]pentan-yl benzoate (AB; AB/Mg=0.03 mol/mol) and 9,9-bis-methoxymethyl-fluorene (Flu; Flu/Mg=0.1 mol/mol). The reaction mixture was kept for 60 min (stage I of catalyst preparation). Then the stirring was stopped and the solid substance was allowed to settle. The supernatant was removed by decanting, after which the solid product was washed with chlorobenzene (125 ml) at 100° C. for 20 min. Then the washing solution was removed by decanting, after which a mixture of titanium tetrachloride (62.5 ml) and chlorobenzene (62.5 ml) was added. The temperature of reaction mixture was increased to 115° C. Then the reaction mixture was kept at 115° C. for 30 min (stage II of catalyst preparation). After which the stirring was stopped and the solid substance was allowed to settle. The supernatant was removed by decanting, after which a mixture of titanium tetrachloride (62.5 ml) and chlorobenzene (62.5 ml) was added. The reaction mixture was kept at 115° C. for 30 min (stage III of catalyst preparation), after which the solid substance was allowed to settle. The supernatant was removed by decanting and the solid was washed five times using 150 ml of heptane at 60° C., after which the catalyst component, suspended in heptane, was obtained.

Table 1 below shows an overview of the addition of the activator and the internal donor for the examples above as well as the ratio between these components and the stage of addition. Table 2 below shows the catalyst composition (in wt %) in the catalyst components as obtained after step C. Table 3 shows the results for the polymerization experiments discussed above under step E.

The mol % of AB in the feed is calculated as ABmol %=AB/(AB+Flu)*100%. The AB/Flu ratio in catalyst (as measured by GC) is calculated from the AB and Flu contents found in the catalyst by GC; the AB/Flu ratio is given as AB % (with AB+Flu=100%, so AB %=AB/(AB+Flu)*100%), molar percentage.

TABLE 1a

Catalyst preparation - part 1.

| Ex. # | AB/Flu | AB Mol % | Flu | Type activator (ACT) |
|---|---|---|---|---|
| 1 | 0.18 | 15.6 | 84.4 | BA-2Me |
| 2 | 0.20 | 16.4 | 83.6 | BA-2Me |
| 3 | 0.24 | 19.2 | 80.8 | BA-2Me |
| 4 | 0.31 | 23.8 | 76.2 | BA-2Me |
| 5 | 0.35 | 25.8 | 74.2 | BA-2Me |
| CE1 | 0.00 | 0.0 | 100.0 | BA-2Me |
| CE2 | 1.00 | 50.0 | 50.0 | BA-2Me |
| CE3 | n.a. | 100.0 | 0.0 | BA-2Me |
| 6 | 0.30 | 23.1 | 76.9 | EB |
| CE4 | 0.30 | 23.1 | 76.9 | EB |
| 7 | 0.20 | 16.4 | 83.6 | EB |

TABLE 1b

Catalyst preparation - part 2.

In procatalyst

| Ex. # | AB Mol % | Flu Mol % | Ti wt % | Mg wt % | Cl wt % | AB wt % | ACT wt % | Flu wt % | EtO⁻ wt % |
|---|---|---|---|---|---|---|---|---|---|
| 1 | 9.5 | 90.5 | 2.26 | 21.2 | 66.1 | 1.1 | 1.1 | 8.2 | 0.9 |
| 2 | 11.0 | 89.0 | 2.40 | 21.3 | 67.8 | 1.5 | 0.8 | 9.5 | 1.1 |
| 3 | 13.9 | 86.1 | 2.59 | 21.8 | 68.3 | 2.4 | 1.2 | 11.6 | 1.8 |
| 4 | 10.6 | 89.4 | 2.46 | 22.4 | 67.9 | 1.2 | 1.1 | 7.9 | 1.1 |
| 5 | 21.1 | 78.9 | 2.35 | 21.4 | 68.4 | 2.6 | 0.6 | 7.6 | 0.8 |
| CE1 | 0.0 | 100 | 2.46 | 20.7 | 65.4 | 0.0 | 1.2 | 12.4 | 1.0 |
| CE2 | 32.9 | 67.1 | 2.19 | 20.2 | 64.3 | 3.2 | 0.7 | 5.1 | 1.5 |
| CE3 | 100.0 | 0.0 | 2.40 | 20.7 | 66.9 | 6.8 | 0.4 | 0.0 | 0.4 |
| 6 | 20.4 | 79.6 | 2.40 | 19.4 | 56.3 | 3.4 | 4.7 | 10.4 | 3.4 |
| CE4 | n.d. | n.d. | 2.6 | n.d. | n.d. | 2.0 | n.d. | n.d. | n.d. |
| 7 | 17.5 | 82.5 | 2.57 | 19.7 | 65.5 | 2.2 | 4.4 | 8.1 | 2.4 |

TABLE 2

| Ex. # | PP Yield (kg/g · cat) | XS total (wt. %) | Bulk Density (g/L) | MFR in g/10 min | Mw/Mn |
|---|---|---|---|---|---|
| 1 | 12.1 | 1.5 | 418 | 10.0 | 5.5 |
| 2 | 13.9 | 2.7 | 411 | 12.9 | 5.2 |
| 3 | 13.1 | 2.8 | 428 | 11.9 | 6.4 |
| 4 | 8.8 | 2.4 | 445 | 11.1 | 6.4 |
| 5 | 13.7 | 2.5 | 444 | 11.4 | 6.4 |
| CE1 | 22.8 | 1.8 | 339 | 14.6 | 5.7 |
| CE2 | 6.9 | 1.9 | 419 | 5.7 | 6.8 |
| CE3 | 16.7 | 3.7 | 427 | 2.8 | 9.7 |
| 6 | 7.0 | n.d. | 366 | 8.0 | 6.4 |
| CE4 | 10.8 | 2.2 | n.d. | 4.3 | 6.2 |
| 7 | 14.1 | 3.0 | 391 | 9.0 | 6.3 |

The effect of butyl Grignard versus phenyl Grignard may be observed by comparing Example 6 (butyl Grignard) with CE4 (phenyl Grignard). It may be observed that although the PP yield is somewhat lower for butyl Grignard (7.0 versus 10.8), the MFR is significantly higher (8.0 versus 4.3).

The effect of EB versus BA-2Me as activator may be observed comparing Example 2 (BA-2Me) and Example 7 (EB). The ethoxy content for Example 7 is higher using EB.

Moreover, the activator content is higher for Example 7 using EB, this also leads to an lowering of the MFR from 12.9 to 9.0.

When no AB is present, ratio AB/Flu=0 this leads to a higher MFR as can be observed from comparing Example 1 with CE1 (10.0 compared to 14.6).

When the ratio AB/Flu is too high (CE2) of when no Flu is present (CE3) this leads to too high Mw/Mn ratio as can be observed from comparing Example 5 with CE2 and CE3, having a Mw/Mn ratio of 6.4 versus 6.9 and even 9.7.

Abbreviations and Measuring Methods:
PP yield (in kg/gcat) is the amount of polypropylene obtained per gram of catalyst component;
XS total (in wt %) is the amount of xylene solubles, measured according to ASTM D 5492-10;
MFR (in g/10 minutes) is the melt flow rate, measured at 230° C. with 2.16 kg load, measured according to ISO 1133:2005;
Mw/Mn is the molecular weight distribution (PDI). The Mw and Mn were determined by Waters 150° C. gel permeation chromatograph combined with a Viscotek 100 differential viscosimeter. The chromatograms were run at 140° C. using 1,2,4-trichlorobenzene as a solvent with a flow rate of 1 ml/min. The refractive index detector was used to collect the signal for molecular weights.
bulk density: the mass of particles of the polymer divided by the total volume these particles occupy. It is measured according to ASTM D 1895-96(2010)e1.
GC analysis was performed by quenching a 100 mg catalyst sample with 10 mL of 0.1 M HCl solution in water and 10 mL of acetonitrile. The organic layer was injected into the GC column, which was kept at 300° C. on a HP 5790 machine with an apolar column. The organic contents (wt. %) were calculated by using the calibration lines of each individual organic compound at high purity (>98%).

Although the invention has been described in detail for purposes of illustration, it is understood that such detail is solely for that purpose and variations can be made therein by those skilled in the art without departing from the spirit and scope of the invention as defined in the claims. It is further noted that the invention relates to all possible combinations of features described herein, preferred in particular are those combinations of features that are present in the claims. It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention claimed is:

1. A process for preparing a procatalyst for polymerization of olefins, said process comprising contacting a magnesium-containing support with a halogen-containing titanium compound, a first internal electron donor represented by Formula A, a second internal electron donor represented by Formula B, and an activator; wherein the molar ratio of the first internal electron donor to the second internal electron donor is between 0.01 and 0.7;

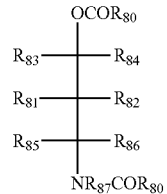

Formula A

-continued

Formula B

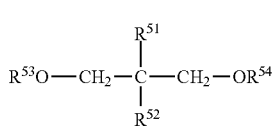

wherein in Formula A each $R^{80}$ group is independently a substituted or unsubstituted aromatic group; $R^{81}$, $R^{82}$, $R^{83}$, $R^{84}$, $R^{85}$, $R^{86}$ and $R^{87}$ are each independently selected from a hydrogen or a hydrocarbyl group; N is a nitrogen atom; O is an oxygen atom; and C is a carbon atom;

wherein in Formula B $R^{51}$ and $R^{52}$ are each independently selected from a hydrogen or a hydrocarbyl group; $R^{53}$ and $R^{54}$ are each independently selected from hydrogen, a halide or a hydrocarbyl group; O is an oxygen atom; and C is a carbon atom; and wherein said process comprises the steps of:
i) contacting a compound $R^4_z MgX^4_{2-z}$ with an alkoxy- or aryloxy-containing silane compound to give a first intermediate reaction product, being a solid $Mg(OR^1)_x X^1_{2-x}$, wherein $R^1$ is a hydrocarbyl group, wherein $R^4$ is butyl; wherein $X^4$ and $X^1$ are each independently a halide; z is in a range of larger than 0 and smaller than 2, being 0<z<2;
ii) optionally contacting the solid $Mg(OR^1)_x X^1_{2-x}$ obtained in step i) with at least one activating compound selected from the group formed by activating electron donors and metal alkoxide compounds of formula $M^1(OR^2)_{v-w}(OR^3)_w$ or $M^2(OR^2)_{v-w}(R^3)_w$, to obtain a second intermediate product; wherein: $M^1$ is a metal selected from the group consisting of Ti, Zr, Hf, Al or Si; v is the valency of $M^1$; $M^2$ is a metal being Si; v is the valency of $M^2$; $R^2$ and $R^3$ are each independently a hydrocarbyl group; w is smaller than v; and
iii) contacting the first or second intermediate reaction product, obtained respectively in step i) or ii), with the halogen-containing Ti-compound, the first internal electron donor according to Formula A, the second internal electron donor according to Formula B, and the activator,
wherein the activator comprises a benzamide activator according to Formula D:

Formula D

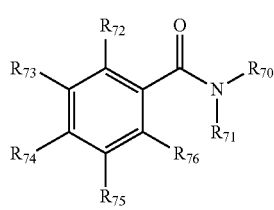

wherein $R^{70}$ and $R^{71}$ are each independently selected from hydrogen or an alkyl; wherein $R^{72}$, $R^{73}$, $R^{74}$, $R^{75}$, $R^{76}$ are each independently selected from hydrogen, a heteroatom, or a hydrocarbyl group.

2. The process according to claim 1, wherein the first internal electron donor according to Formula A is selected from the group consisting of 4-[benzoyl(methyl)amino]pentan-2-yl benzoate; 2,2,6-tetramethyl-5-(methylamino)heptan-3-ol dibenzoate; 4-[benzoyl (ethyl)amino]pentan-2-yl benzoate and 4-(methylamino)pentan-2-yl bis (4-methoxy) benzoate).

3. The process according to claim 1, wherein the second internal electron donor according to Formula B is selected from the group consisting of 2-isobutyl-2-isobutyl-1,3-dimethoxypropane, 2-ethyl-2-butyl-1,3-dimethoxypropane, 2-isopropyl-2-isopentyl-1,3-dimethoxypropane and 9,9-bis-methoxymethyl-fluorene.

4. The process according to claim 1, wherein the first internal electron donor is 4-[benzoyl(methyl)amino]pentan-2-yl benzoate and wherein the second internal electron donor is 9,9-bis-methoxymethyl-fluorene.

5. The process according to claim 1, wherein the ratio between the first internal electron donor and the second internal electron donor is between 0.05 and 0.65.

6. The process according to claim 1, wherein the first internal electron donor is 4-[benzoyl(methyl)amino]pentan-2-yl benzoate and wherein the second internal electron donor is 9,9-bis-methoxymethyl-fluorene and the activator is N,N-dimethylbenzamide and wherein the ratio between the first internal electron donor and the second internal electron donor is between 0.3 and 0.5.

7. The process according to claim 1, comprising the steps of:
i) contacting butylmagnesiumchloride with tetraethoxysilane to give said first intermediate reaction product;
ii) contacting said first intermediate reaction product with ethanol as activating electron donor and titanium tetraethoxide as metal alkoxide compounds to obtain a second intermediate reaction product; and
iii) contacting the second intermediate reaction product with titanium tetrachloride, 4-[benzoyl(methyl)amino] pentan-2-yl benzoate as the first internal electron donor, 9,9-bis-methoxymethyl-fluorene as the second internal electron donor, and N,N-dimethylbenzamide as the activator.

8. The process according to claim 7, wherein step iii) comprises three stages I, II and III of adding titanium tetrachloride and wherein 4-[benzoyl(methyl)amino]pentan-2-yl benzoate, 9,9-bis-methoxymethyl-fluorene, and activator are each added during stage I.

9. The process according to claim 7, wherein step iii) comprises three stages I, II and III of adding titanium tetrachloride and wherein the activator is added during stage I, 4-[benzoyl(methyl)amino]pentan-2-yl benzoate is added during stage II, and 9,9-bis-methoxymethyl-fluorene is added during stage III.

10. A procatalyst obtained by a process according to claim 1.

11. A catalyst system for the polymerization of olefins, comprising a procatalyst according to claim 10; a co-catalyst; and an external donor.

12. A process for preparing a polyolefin the process comprising contacting an olefin with the catalyst system according to claim 11.

13. The process according to claim 1, wherein
v is 3 or 4;
said activator is a benzamide selected from the group consisting of benzaethyl benzoate, benzoyl chloride, ethyl p-bromobenzoate, n-propyl benzoate, and benzoic anhydride, benzamide, N-methylbenzamide, N-ethylbenzamide, N,N-dimethylbenzamide, N,N-dimethylbenzamide, and N-methyl-N-ethylbenzamide; and
the ratio between the first internal electron donor and the second internal electron donor is between 0.2 and 0.55.

14. The process according to claim 12, wherein the olefin is propylene.

15. The process according to claim 1, $R^{70}$ and $R^{71}$ are each independently an alkyl.

16. A process for preparing a procatalyst for polymerization of olefins, said process comprising contacting a magnesium-containing support with a halogen-containing titanium compound, a first internal electron donor represented by Formula A, a second internal electron donor represented by Formula B, and an activator; wherein the molar ratio of the first internal electron donor to the second internal electron donor is between 0.01 and 0.7;

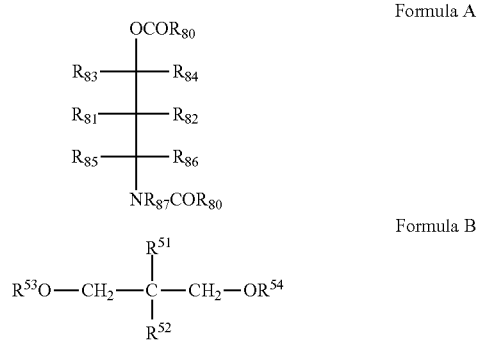

Formula A

Formula B wherein in Formula A each $R^{80}$ group is independently a substituted or unsubstituted aromatic group; $R^{81}$, $R^{82}$, $R^{83}$, $R^{84}$, $R^{85}$, $R^{86}$ and $R^{87}$ are each independently selected from a hydrogen or a hydrocarbyl group; N is a nitrogen atom; O is an oxygen atom; and C is a carbon atom; and wherein in Formula B $R^{51}$ and $R^{52}$ are each independently selected from a hydrogen or a hydrocarbyl group; $R^{53}$ and $R^{54}$ are each independently selected from hydrogen, a halide or a hydrocarbyl group; O is an oxygen atom; and C is a carbon atom;

wherein said process comprises the steps of:
i) contacting a compound $R^4{}_z MgX^4{}_{2-z}$ with an alkoxy- or aryloxy-containing silane compound to give a first intermediate reaction product, being a solid $Mg(OR^1)_x X^1{}_{2-x}$, wherein $R^1$ is a hydrocarbyl group, wherein $R^4$ is butyl; wherein $X^4$ and $X^1$ are each independently a halide; z is in a range of larger than 0 and smaller than 2, being 0<z<2;
ii) optionally contacting the solid $Mg(OR^1)_x X^1{}_{2-x}$ obtained in step i) with at least one activating compound selected from the group formed by activating electron donors and metal alkoxide compounds of formula $M^1(OR^2)_{v-w}(OR^3)_w$ or $M^2(OR^2)_{v-w}(R^3)_w$, to obtain a second intermediate product; wherein: $M^1$ is a metal selected from the group consisting of Ti, Zr, Hf, Al or Si; v is the valency of $M^1$; $M^2$ is a metal being Si; v is the valency of $M^2$; $R^2$ and $R^3$ are each independently a hydrocarbyl group; w is smaller than v; and
iii) contacting the first or second intermediate reaction product, obtained respectively in step i) or ii), with the halogen-containing Ti-compound, the first internal electron donor according to Formula A, the second internal electron donor according to Formula B, and the activator, wherein the activator comprises a monoester activator according to Formula C'

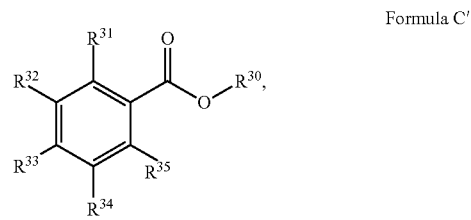

Formula C' wherein $R^{30}$ is a hydrocarbyl group, and $R^{31}$, $R^{32}$, $R^{33}$, $R^{34}$, and $R^{35}$ are each independently selected from hydrogen, a heteroatom, or a hydrocarbyl group; and wherein the procatalyst provides an olefin polymerization product having a molecular weight distribution of 4.5 and 6.5.

17. The process according to claim 16, comprising the steps of:
i) contacting butylmagnesiumchloride with tetraethoxysilane to give said first intermediate reaction product;
ii) contacting said first intermediate reaction product with ethanol as activating electron donor and titanium tetraethoxide as metal alkoxide compounds to obtain a second intermediate reaction product; and
iii) contacting the second intermediate reaction product with titanium tetrachloride, 4-[benzoyl(methyl)amino] pentan-2-yl benzoate as the first internal electron donor, 9,9-bis-methoxymethyl-fluorene as the second internal electron donor, and ethylbenzoate as the activator.

18. The process according to claim 16, wherein
v is 3 or 4;
said activator is a monoester selected from the group consisting of butyl formate, ethyl acetate, amyl acetate, butyl acetate, ethyl acrylate, methyl methacrylate, isobutyl methacrylate, ethyl p-methoxy benzoate, methyl p-ethoxybenzoate, ethyl p-ethoxybenzoate, ethyl benzoate, methyl benzoate, propyl benzoate, ethyl p-chlorobenzoate, ethyl p-bromobenzoate, methyl-p-toluate ethyl-naphthate, ethyl acetate; and
the ratio between the first internal electron donor and the second internal electron donor is between 0.2 and 0.55.

19. The process according to claim 16, wherein the first internal electron donor is 4-[benzoyl(methyl)amino]pentan-2-yl benzoate and wherein the second internal electron donor is 9,9-bis-methoxymethyl-fluorene and the activator is ethylbenzoate and wherein the ratio between the first internal electron donor and the second internal electron donor is between 0.3 and 0.5.

* * * * *